United States Patent
Lanquetin et al.

(10) Patent No.: US 6,831,073 B1
(45) Date of Patent: Dec. 14, 2004

(54) HORMONAL COMPOSITION CONSISTING OF AN OESTROGEN COMPOUND AND OF A PROGESTATIONAL COMPOUND

(75) Inventors: Michel Lanquetin, La Trinite (FR); Jacques Paris, Nice (FR); Jean-Louis Thomas, Charenton-le-Pont (FR)

(73) Assignee: Laboratoire Theramex (MC)

( * ) Notice: Subject to any disclaimer, the term of this patent is extended or adjusted under 35 U.S.C. 154(b) by 0 days.

(21) Appl. No.: 09/284,147

(22) PCT Filed: Oct. 8, 1997

(86) PCT No.: PCT/FR97/01792

§ 371 (c)(1),
(2), (4) Date: May 17, 1999

(87) PCT Pub. No.: WO98/15279

PCT Pub. Date: Apr. 16, 1998

(30) Foreign Application Priority Data

Oct. 8, 1996 (FR) .......................................... 96 12239

(51) Int. Cl.$^7$ .............................. A61K 31/56; C07J 1/00
(52) U.S. Cl. ...................... 514/169; 514/170; 514/171; 514/177; 514/178; 514/182; 552/625
(58) Field of Search ................................ 514/169, 170, 514/171, 177, 178, 182; 552/625

(56) References Cited

U.S. PATENT DOCUMENTS

| | | | | |
|---|---|---|---|---|
| 5,565,443 A | * | 10/1996 | Lanquetin et al. | 514/169 |
| 5,843,934 A | * | 12/1998 | Simpkins | 514/182 |
| 5,888,543 A | * | 3/1999 | Gast | |
| 5,891,867 A | * | 4/1999 | Lanquetin et al. | 514/170 |
| RE36,247 E | * | 7/1999 | Plunkett et al. | 514/170 |

OTHER PUBLICATIONS

Stiruk–Ware, English translation of Rev. Pat (1995), 45(19), pp. 2401–2406.*
Fraser et al. (Medline, DN 89261206, abstract of Maturitas, (Mar. 1989), 11(1), 21–34).*
Cano et al. (CA 115:150824, abstract of Maturitas (1991), 13(1), 35–42).*
Blanc et al. (1998:856197, SCISEARCH, abstract of Clinical Therapeutics, (1998), vol. 20 (5), pp 901–912.*
Sitruk–Ware, (DN 96148040, abstract of Rev. Du Prat (1995) 45 (19), p–2401–6).*
Catherino, WIlliam et al. (DN 124:21954, HCAPLUS, abstract of J. Steroid Biochem. Mol. Biol. (1995), 55(2), 239–46).*
Conard et al "Cardiovascular . . . Estradiol", Fertility and Sterility, vol. 64, No. 5, 1995, pp. 957–962.
Sitruk–Ware, "Pharmacology . . . Contraceptives", Rev. Pat., Dec. 1, 1995, vol. 45, No. 19, pp. 2401–2406.

* cited by examiner

*Primary Examiner*—Sabiha Qazi
(74) *Attorney, Agent, or Firm*—Dennison, Schultz, Dougherty & MacDonald

(57) ABSTRACT

A method of treating estrogenic deficiencies in women while further avoiding the appearance of osteoporosis, withdrawal bleeding and cardiovascular diseases in post-menopausal women without any androgenic effect, and no deleterious effects on blood vessels comprising continuously without interruption administering to said women, a combination of 0.5 to 3 mg of an estrogenic compound and 1.5 to 3.75 mg of nomegestrol acetate.

6 Claims, No Drawings

HORMONAL COMPOSITION CONSISTING OF AN OESTROGEN COMPOUND AND OF A PROGESTATIONAL COMPOUND

This application is a 371 a PCT/FR97/01792 filed Oct. 8, 1997.

The present invention relates to the field of therapeutic chemistry and more particularly to the field of hormonal pharmaceutical techniques.

A more precise subject of the invention is new pharmaceutical compositions formed by an estroprogestative combination with a view to the correction of estrogenic deficiencies in natural or artificial menopauses or in order to stop ovulation in women during their period of ovarian activity.

In particular a subject of the invention is an estroprogestative combination, characterized in that it is constituted by unit doses containing the combination of a progestative and an estrogen, the two components being present simultaneously in each medicinal dose.

This combination is intended to be administered by oral route.

As is known, the life expectancy of women has passed in less than a century from 50 to 80 years, whilst the average age for the onset of the menopause has remained unchanged. Therefore, women spend a third of their life in a state of estrogenic deficiency which is the origin of the increase in risk of osteoporosis and cardiovascular illnesses. Sequential replacement treatment for the menopause cures the climateric symptomology and prevents osteoporosis and the onset of illnesses. It creates artificial cycles which are followed by a withdrawal bleeding. This therapeutic schema quite particularly suits women for whom the menopause is recent but it is not always well accepted in the long term, which in part explains the poorer observance of treatment (DRAPIER FAURE E.; Gynècologie. 1992, 43: 271–280).

In order to overcome this drawback, combined combinations have been perfected where the two components are taken simultaneously, the progestative having the effect of permanently opposing the proliferative action of the estrogen on the endometrium, by creating an atrophy of the endometrium and as a consequence, the absence of withdrawal bleeding (HARGROVE J. T., MAXSON W. S., WENTZ A. C., BURNETT L. S., Obstet Gynecol, 1989, 73: 606–612).

This "no periods" schema more particularly suits women for whom the menopause is already well in the past. It can be prescribed in courses of sequential combinations in order to improve the long-term observance of replacement hormone treatment for the menopause.

The dose of progestative to be used in a combined replacement treatment is in general deduced from that which is usually prescribed in sequential schemata. In the latter the dose chosen is that which gives over the long term less than 1% endometrial hyperplasia when the progestative is administered discontinuously, more than 10 days per cycle, in post-menopasual women under replacement estrogenotherapy (WHITEHEAD et al., J. reprod. Med, 1982, 27: 539–548, PATERSON et al, Br Med J, Mar. 22, 1980, 822–824).

In the combined treatment, these same progestatives were used at half the dose judged to be effective during a sequential treatment: this is the example of the micronized progesterone, didrogesterone (FOX H., BAAK J., VAN DE WEIJER P., AL-AZZAWI E., PATERSON M., JOHNSON A., MICHELL G., BARLOW D., FRANCIS R., 7th International Congress on the Menopause, Stockholm, Jun. 20–24, 1993, abstr 119) and medroxyprogesterone acetate (BOCANERA R, BEN J., COFONE M., GUINLE I., MAILAND D., SOSA M., POUDES G., ROBERTI A., BISO T., EZPELETA D., PUCHE R., TOZZINI R., 7th International Congress on the Menopause, Stockholm, Jun. 20–24, 1993, abstr 40) which were used at doses of 100, 10 and 5 mg/day respectively, with encouraging results on the clinical and endometrial level. Among the progestatives, nomegestrol acetate appeared to be one of the most effective. Nomegestrol acetate is a non-androgenic progestative derived from 19-nor progesterone, its use in sequential administration during the menopause at the dose of 5 mg/day, 12 days per cycle, in combination with different types of estrogens, allows endometrial hyperplasia to be prevented as shown by a multicentre study on 150 women for one year (THOMAS J. L., BERNARD A. M., DENIS C., 7th International Congress on the Menopause, Stckholm, Jun. 20–24, 1993, abstr 372).

The absence of hyperplasia was confirmed in a study where the nomegestrol acetate was administered at the same dose, 14 days per cycle, in women treated with percutaneous estradiol (BERNARD A. M. et al. Comparative evaluation of two percutaneous estradiol gels in combination with nomegestrol acetate in hormone replacement therapy. XIV World Congress of Gynecology and Obstetrics, FIGO, Montreal, Sep. 24–30, 1994).

The combined treatment is more often used in a continuous fashion, i.e. without interruption. However some people are in favour of using it in an intermittent fashion, for example 25 days per month (BLRKAUSER M. ET AL; Substitution hormonale: une indication bien posèe et des schèmas de traitement individuels sont dèterminants pour le succès du traitement, Mèd. et Hyg., 1995, 53: 1770–1773). The aim of the therapeutic interruption is to remove the inhibition exercised by the progestative on the synthesis of the estradiol and progesterone receptors and in this way to avoid the lowering of receptivity of the hormono-dependant tissues.

The progesterone used according to the present invention is nomegestrol acetate which is active by oral route. The estrogen used is free or esterified estradiol, or conjugated equine estrogens which are presented according to a formulation which is active by oral route and in particular estradiol valerate. Nomegestrol acetate and free or esterified estradiol or conjugated equine estrogens are administered in one of the forms which permit administration by oral route: gelatine capsules, capsules, pills, sachets of powder, tablets, coated tablets, sugar-coated tablets etc.

The present invention is characterized in that it is constituted by a new estroprogestative combination, which is active by oral route and administered in a combined manner. A subject of the present invention is also its use in the correction of estrogenic deficiencies, in the prevention of osteoporosis and cardiovascular illnesses in post-menopausal women, or in stopping ovulation in women during their period of ovarian activity.

The compositions according to the invention based on nomegestrol and free or esterified or equine conjugated estrogens are administered in a continuous fashion or intermittent fashion from 21 to 25 days per month.

According to a particular implementation of the invention the compositions contain a quantity of nomegestrol acetate ranging form 1.5 to 3.75 mg and a quantity of free or esterified estradiol or conjugated estrogens ranging from 0.5 to 3 mg. Preferably, the optimal formulations contain 2.5 mg of nomegestrol acetate combined with: either 1.5 mg of free estradiol or 2 mg of estradiol ester or 0.625 mg of conjugated equine estrogens, per daily dose.

This combined administration method can have several therapeutic indications. In post-menopausal women, the estroprogestative combination is intended to compensate for the functional disorders brought about by hypoestrogenism of the menopause, while maintaining an atrophy of the endometrium and avoiding in a majority of them the appearance of withdrawal bleeding.

In women during the period of ovarian activity, young or in the years preceding the menopause, the cyclic administration of the hormonal combination is capable of stopping ovulation and of exercising a contraceptive effect insofar as it has been proved that nomegestrol is capable of stopping the ovulation peak of LH and FSH, starting from 1.25 mg/day (BAZIN B. et al, Effect of nomegestrol acetate, a new 19-norprogesterone derivative on pituitary ovarian function in women. Br. J. Obstet. Gynaecol., 1987, 94: 1199–1204). When the hormonal combination is given for a contraceptive purpose, the aim of nomegestrol acetate is to stop ovulation and for the estrogenic compound to compensate for hypoestrogenia and ensure a better control of the cycle.

A subject of the present invention is also a process for obtaining new pharmaceutical compositions.

The obtaining process according to the invention consists of mixing the active ingredients: nomegestrol acetate and free or esterified estradiol or conjugated equine estrogens with one or more pharmaceutically acceptable, non-toxic, inert excipients.

Among the excipients which can be mentioned are binding and solubilizing agents, compression agents, disintegration agents and slip agents. This mixture can be subjected to direct compression or to several stages of compression in order to form tablets which, if desired, can have their surface protected by a film, by lacquering or coating. The production of tablets by direct compression allows a maximum reduction in the proportion of diluting agents, binding agents, disintegration agents and slip agents. The production of gelatine capsules can be carried out by mixing the active ingredients with an inert diluant and a slip agent. The tablets contain, in particular, mass diluting agents such as lactose, sorbitol for direct compression, marketed under the name NEOSORB 60, Palatinite which is a registered trademark for designating an equimolar mixture of the isomer of -D-glucopyranosido 1,6-mannitol and -D-glucopyranosido 1,6-glucitol crystallized with two molecules of water, mannitol, sorbitol or the mixture lactose/PVP sold under the name Ludipress. The compression binding agents are in general microcrystalline celluloses such as those sold under the name AVICEL PH 101 or AVICEL PH 102. The polyvinylpyrrolidone plays an important role and facilitates the agglomeration of the powders and the compressibility of the mass. To this end polyvinylpyrrolidones are used with a molecular weight comprised between 10000 and 30000 such as Povidone, Kollidon of a grade comprised between 12 and 30. The mixture also contains slip or anti-electrostatic agents so that the powder does not agglomerate in the feed hoppers. In this respect, colloidal silicas can be mentioned which are sold under the name AEROSIL 100 or AEROSIL 200. The mixture also contains disintegration agents which allow disintegration or crumbling which conforms to pharmaceutical standards. There can be mentioned as useful disintegration agents, polymers of cross-linked vinylpyrrolidones such as those sold under the names Polyplasdone or Polyclar AT, carboxymethylamidons such as those sold under the names Amigel or Explotab, cross-linked carboxymnethylcelluloses or croscarmelloses such as the compound sold under the name AC-DI-SOL> In addition, the preparation contains lubrication agents which facilitate the compression and ejection of the tablet from the tablet compressing machine. There can be mentioned as lubrication agents, glycerol palmitostearate sold under the name Precirol, magnesium stearate, stearic acid or talc. After compression the tablets can be coated in order to ensure their storage or to facilitate their deglutination. The coating agents are either of cellulose origin such as cellulose phthalate (Sepifilm, Pharmacoat), or of polyvinyl origin of Sepifilm ECL type, or of saccharose origin such as the sugar for sugar-coating of Sepisperse DR, AS, AP OR K (coloured) type. The tablets, whether coated or not, can in addition, be surface or bulk coloured, by plant or synthetic colouring agents (for example chinolin yellow lacquer or E 104). The proportions of the different constituents varies according to the type of tablet to be produced. The content of active ingredients can vary from 1.5 to 3.75 mg for nomegestrol acetate and from 0.5 to 3 mg for free or esterified estradiol or for conjugated equine estrogens. The dilution agents vary from 20 to 75% of the total mass, the slip agents from 0.1 to 2% of the total mass, the compression binding agents vary from 2 to 20%, the polyvinylpyrrolidone from 0.5 to 15%, the disintegration agents vary from 2 to 5.5% for the cross-linked polyvinylpyrrolidone or the carboxymethylamidon, from 2.0 to 3.0% for the croscarmellose. The quantities of lubricating agents vary as function of the type of agents from 0.1 to 3.0%.

The compositions according to the invention are intended to be administered once per day. However, depending on the therapeutic requirements, administration can be split up (twice per day) or on the other hand, repeated (two tablets per day). The following examples illustrate the invention. They in no way limit it.

EXAMPLE I

| Tablets with 4 mg of active ingredient | |
|---|---|
| Active ingredients: | |
| estradiol | 1.5 mg |
| nomegestrol acetate | 2.5 mg |
| Microcrystalline cellulose | 22.4 mg |
| (marketed under the name AVICEL PH 102) | |
| Lactose | 60 mg |
| Polyvinylpyrrolidone | 8.4 mg |
| Colloidal silica | 1.2 mg |
| Glycerol palmitostearate | 3.6 mg |
| Colouring agent E.104 | 0.4 mg |
| for a tablet completed at an average weight of 100 mg. | |

EXAMPLE II

Study of the clinical tolerance during two continuous combined schemata of hormone replacement therapy for the menopause The pilot study is carried out over 24 weeks on two parallel groups subjected to treatments A and C:

Treatment A

Nomegestrol acetate 2.5 mg/day every day+percutaneous 17β-estradiol 1.5 mg/day every day.

The nomegestrol acetate is administered in the form of tablets and the percutaneous 17β-estradiol in the form of a gel.

Treatment C

Nomegestrol acetate 2.5 mg/day every day+estradiol valerate 2 mg/day every day.

The estradiol valerate is administered in the form of tablets.

The pilot study is intended to evaluate the endometrial clinical tolerance during the use of the two hormone replacement therapy schemata for the menopause so-called "without periods" combing in a continuous combined fashion treatment A or C. The endometrial clinical tolerance is evaluated from the presence or not of occurences of vagina bleeding, their intensity, their frequency, from data acquired from endovaginal echographical examination etc.

Also, another aim of this study is to assess the general clinical tolerance (weight, blood pressure, mammary symptoms), biological tolerance (Formule Numeration Sanguine (blood count), glycemia, cholesterol . . . ), as well as the observance of treatment.

The selection of subjects is carried out as a function of "inclusion" criteria. These criteria are to do:

with the menopause:
women over 50 years old are included who have had a natural menopause expressed clinically by an amenorrhea greater than 12 months and less than 10 years, the women having had a natural menopause confirmed biologically by quantitative analysis of FSH (Follicle stimulating hormone) and estradiol (i.e. plasmatic FSH$\geq$20 IU/I, plasmatic E$_2 \leq$0.11 nmol/l).

with women:
women who have not had hysterectomies are included, whose Quetelet's index (weight in kg/(height in m)$^2$) is $\leq$27, having had regular cycles before the menopause, having never received hormone replacement therapy for the menopause or having had a clinically well tolerated hormone replacement therapy (absence of abnormal bleeding), interrupted for more than 6 weeks, presenting an endometrial thickness measured by endovaginal echography $\leq$5 mm, accepting the idea of hormone replacement therapy for the menopause, who would like a hormone therapy without periods, justifying an estroprogestative hormone therapy for at least 6 months, cooperative: accepting to conform to the requirements of the study, whose psychic and intellectual profile would allow one to suppose a good observance of the treatment, having a mammograph dating from less than a year from the date of inclusion. At the start of treatment the patients undergo an inclusion consultation ($C_1$) the purpose of which is to verify that the inclusion criteria have been respected, that the endovaginal echograph is normal and to obtain the written consent of the patient as regards participation. The intermediate consultation ($C_2$) takes place between the 9th and 11th week of treatment, the purpose of which is to verify mammary and endometrial clinical tolerance is good as regards the treatment.

Lastly, a final consultation ($C_3$) takes place during the 24th week of treatment.

The patients who wish to continue the study can receive, for 24 additional weeks, the estroprogestative treatment received during the study according to the same therapeutic schema. The extension of the study thus allows a complete monitoring of the study over 48 weeks.

ANALYSIS OF THE STUDY

RESULTS I

The attached Tables I and II, reveal a difference in terms of the amenorrhea results (i.e. no bleeding from 0 to 24 weeks) and of mammary and/or endometrial tolerance as a function of the estrogen.

TABLE I

Treatment A
Nomegestrol acetate + percutaneous 17β-estradiol

| Elapse since menopause ameno/month | Presence of HRT previously | Start of treatment | Duration of treatment weeks | Endometrial thickness before/after mm | COMMENTS |
|---|---|---|---|---|---|
| 72 | no | 17.10.94 | 24<br>24 ext | 2/2 | amenorrhea<br>endometrial thickness after 48 weeks of treatment = 2 mm |
| 82 | no | 04.11.94 | 24<br>extension | 3/3 | amenorrhea |
| 26 | yes<br>well tolerated | 09.01.95 | 24<br>extension | 3/3 | amenorrhea |
| 108 | no | 16.01.95 | 24<br>extension | 1/4 | amenorrhea |
| 48 | no | 13.02.95 | 24 | 3/2 | 1 episode of bleeding at 42 days (a few drops) between the 1st and 6th weeks; breast tension and pain of minimal intensity from the 1st to the 22nd week (7 days/week) Extension not effected: did not pick up the treatment kit owing to holidays; following the same treatment outside protocol |
| 24 | no | 10.03.95 | 24<br>extension | 2/5 | amenorrhea; breast tension and pain of slight intensity 6th to the 12th week (7 days/week) |
| 55 | yes<br>well tolerated | 20.03.95 | 24<br>extension | 4/8 | amenorrhea |
| 27 | yes<br>well tolerated | 08.05.95 | 24 | 3/5 | amenorrhea<br>Extension not effected: did not pick up the treatment kit owing to holidays; same treatment outside protocol |
| 90 | yes<br>well tolerated | 10.04.95 | 24<br>extension | 4/4 | amenorrhea |
| 13 | yes<br>well tolerated | 03.07.95 | 24<br>extension | 1 pending | amenorrhea |
| 99 | yes<br>well tolerated | 24.04.95 | 24<br>extension | 1/4 | amenorrhea |

TABLE I-continued

Treatment A
Nomegestrol acetate + percutaneous 17β-estradiol

| Elapse since menopause ameno/month | Presence of HRT previously | Start of treatment | Duration of treatment weeks | Endometrial thickness before/after mm | COMMENTS |
|---|---|---|---|---|---|
| 21 | yes, well tolerated | 26.06.95 | 24 extension | 4 pending | amenorrhea |
| 96 | ? | 29.05.95 | 24 extension | 2 pending | amenorrhea |
| 65 | yes, well tolerated | 10.05.95 | 24 extension | 1/3 | amenorrhea; 10 episodes (4 days/week) of breast pains of minimal intensity |
| 13 | no | 12.06.95 | stopped at 16 | 3 not measured | continuous slight bleeding from the 5th week until treatment stopped |
| 38 | yes, well tolerated | 10.07.95 | 24 extension | 2 pending | amenorrhea |

EXTENSION = 24 additional weeks of treatment
HRT = hormone replacement therapy

CONCLUSION

Of the 16 patients treated:
1 left the study, i.e. 6%
15 finished the study after 24 weeks, i.e. 94%

13 extensions of treatment (24 additional weeks) 81%
The two extensions which did not take place whee due to reasons which were independent of the treatment, the patients continued the same treatment outside the treatment protocol.

TABLE II

Treatment C
Nomegestrol acetate + estradiol valerate per os

| Elapse since menopause ameno/month | Presence of HRT previously | Start of treatment | Duration of treatment weeks | Endometrial thickness before/after mm | COMMENTS |
|---|---|---|---|---|---|
| 12 | no | 21.11.94 | stopped at 8 | 4/* *= not measured at the control echo | amenorrhea, breast tension and pain of slight intensity from the 2nd week to the 8th week; STOPPED owing to high abdomino-pelvic tension due to Increased size of a sub-serous fibroma: echo before treatment = 37 mm; echo after 8 weeks of treatment = 75 mm |
| 46 | yes, well tolerated | 28.11.94 | 24 extension | 3/6 | 1 episode of bleeding of 31 days between the 5th and the 9th week (a few drops) |
| 31 | yes, well tolerated | 28.11.94 | stopped at 10 | 2 not measured | amenorrhea, STOPPED for insomnia, nervousness and pain in lower limbs |
| 60 | yes, well tolerated | 30.01.95 | 24 extension | 4/2 | amenorrhea, breast tension and pain of slight intensity from the 2nd week of treatment until the 19th week |
| 121 | yes, well tolerated | 06.02.95 | stopped at 9 | 3 not measured | 1 episode of bleeding of 16 days of low intensity from the 6th week<br>breast tension of minimal intensity from the 2nd week to the 8th week; STOPPED owing to headaches, night sweats and a blood pressure of 17/10 |
| 36 | yes, well tolerated | 06.02.95 | 24 | 4* | amenorrhea, 23 episodes of breast tension of high intensity of 7 days/week; extension impossible as estrogen dose reduced due to breast tension |
| 47 | yes, well tolerated | 27.02.95 | 24 extension | 2/2 | amenorrhea; 6 episodes of breast tension and pain of slight intensity (2 days/week) |
| 62 | no | 13.03.95 | 24 extension | 1/4 | amenorrhea |
| 74 | yes, well tolerated | 20.03.95 | 24 extension | 4/6 | amenorrhea |
| 110 | yes, well tolerated | 08.05.95 | stopped at 18 | 2 not measured | amenorrhea until 12 weeks then 1 episode of bleeding of 41 days until treatment stopped |
| 16 | yes, well tolerated | 22.05.95 | 24 extension | 1 pending | amenorrhea |
| 60 | yes, well tolerated | 12.06.95 | stopped at 16 | 2/3 | 4 episodes of bleeding of low intensity (6 days/week)<br>5 episodes of breast pain of medium intensity (6 days/week); STOPPED owing to mastitis and a breast abscess |
| 11 | no | 19.06.95 | 24 extension | 2 pending | 1 episode of bleeding 12 days (a few drops) |
| 38 | yes, well tolerated | 03.07.95 | stopped at 4 | 5 not measured | 1 episode of bleeding of 11 days until treatment stopped of low intensity |

CONCLUSION

Of the 14 patients treated
6 left the study i.e. 43%
8 finished the study after 24 weeks, i.e. 57%
7 extensions of treatment (24 additional weeks), i.e. 50%
% of amenorrhea (i.e. no occurrence of bleeding for 24 weeks)=43%

RESULTS II

A—OBSERVANCE

While no significant difference exists between the two groups A and C, a lower number of days when treatment lapsed over all the 24 weeks of the study was observed with treatment A.

B—ENDOMETRIAL CLINICAL TOLERANCE

The most significant absolute percentage of amenorrhea is found in group A, the difference being significant in phase II (13th to 24th week of treatment) As has been described in the literature, the percentage of amenorrhea increases with time; therefore, for group C, it is 35.3% during the first 12 weeks of treatment, and 46.1% during the last 12 weeks.

The attached tables III, IV and V illustrate the results obtained.

AMENORRHEA

Analysis regarding treatment

TABLE III

Phase I/weeks 1 to 12

|  | TOTAL | | GROUP A | | GROUP C | | |
| --- | --- | --- | --- | --- | --- | --- | --- |
|  | N | % | N | % | N | % | P |
| Amenorrhea | | | | | | | |
| yes | 19 | 37.2% | 9 | 50% | 6 | 35.3% | 0.316 |
| no | 32 | 62.7% | 9 | 50% | 11 | 64.7% | |
| Spotting | | | | | | | |
| yes | 32 | 62.7% | 9 | 50% | 11 | 64.7% | 0.316 |
| no | 19 | 37.2% | 9 | 50% | 6 | 35.3% | |

|  | TOTAL | | GROUP A | | GROUP C | | |
| --- | --- | --- | --- | --- | --- | --- | --- |
|  | N | avg ± week (min:max) | N | avg ± week (min:max) | N | avg ± week (min:max) | P |
| Total duration of bleeding (days) | 51 | 9.1 ± 2.1 0:70 | 18 | 9.1 ± 4.5 0:70 | 17 | 8.9 ± 2.7 0:31 | 0.412 |
| Average intensity | 51 | 0.8 ± 0.1 0:2 | 18 | 0.7 ± 0.2 0:2 | 17 | 0.9 ± 0.2 0:2.5 | 0.446 |
| Number of weeks of bleeding | 51 | 2.1 ± 0.4 0:10 | 18 | 1.8 ± 0.7 0:10 | 17 | 2.1 ± 0.5 0:7 | 0.552 |
| Total number of episodes | 51 | 1.2 ± 0.2 0:6 | 18 | 1 ± 0.3 0:4 | 17 | 1.2 ± 0.4 0:6 | 0.434 |

None of the patients suffered from metrorrhagias during phase I

TABLE IV

Phase II/weeks 13 to 24

|  | TOTAL | | GROUP A | | GROUP C | | |
| --- | --- | --- | --- | --- | --- | --- | --- |
|  | N | % | N | % | N | % | P |
| Amenorrhea | | | | | | | |
| yes | 20 | 42.5% | 12 | 66.7% | 6 | 46.1% | |
| no | 27 | 57.4% | 6 | 33.3% | 7 | 53.8% | 0.006 |
| Spotting | | | | | | | |
| yes | 27 | 57.4% | 6 | 33.3% | 7 | 53.8% | |
| no | 20 | 42.5% | 12 | 66.7% | 6 | 46.1% | 0.006 |

|  | TOTAL | | GROUP A | | GROUP C | | |
| --- | --- | --- | --- | --- | --- | --- | --- |
|  | N | avg ± week (min:max) | N | avg ± week (min:max) | N | avg ± week (min:max) | P |
| Total duration of bleeding (days) | 47 | 13.9 ± 3.1 0:75 | 18 | 6.2 ± 3.3 0:42 | 13 | 18.5 ± 7.7 0:75 | 0.013 |
| Average intensity | 47 | 0.9 ± 0.1 0:2 | 18 | 0.6 ± 0.2 0:2.33 | 13 | 1.0 ± 0.3 0:2 | 0.055 |
| Number of weeks of bleeding | 47 | 2.9 ± 0.6 0:12 | 18 | 1.3 ± 0.6 0:9 | 13 | 3.3 ± 1.2 0:11 | 0.007 |
| Total number of episodes | 47 | 1.3 ± 0.3 0:7 | 18 | 0.6 ± 0.3 0:6 | 13 | 1.1 ± 0.5 0:7 | 0.002 |

None of the patients suffered from metrorrhagias during phase II

TABLE V

| Δ % between C1 and C3 | N | TOTAL avg ± week (min:max) | N | GROUP A avg ± week (min:max) | N | GROUP C avg ± week (min:max) | P |
|---|---|---|---|---|---|---|---|
| A.L.A.T. | 43 | −23.1% ± 5.2% −88.2%:85.7% | 17 | −19.0% ± 3.8% −50%:7.1% | 11 | −31.2% ± 13.2% −88.2%:29.4% | 0.936 |
| F.S.H. | 45 | −74.1% ± 4.9% −98.4%:69.2% | 18 | −72.2% ± 5.5% −98%:24.8% | 12 | −78.2% ± 9.6% −98.4%:22.8% | 0.405 |
| Estradiol (pg/ml) | 40 | 432% ± 68.5% −54%:1640% | 15 | 567% ± 118.7% −16%:1320% | 10 | 609% ± 163.6% −54.3%:1640% | 0.036 |

A.L.A.T. = Alanine Aminotransferase Transaminase
F.S.H. — Follicle Stimulating Hormone The relative variation in estradiol level is quite important in the two groups (Δ%=567% in group A and 609% in group c), p=0.04

Table VI illustrates another study which was carried out. In this other study, it is interesting to note that with nomegestrol acetate, the percentage of patients with absolute amenorrhea (including all forms of estrogenotherapy) is greater from the 3rd month of treatment: 42.5% against 33.3%. In the treatment mentioned above, one must wait until the 12th month of treatment to obtain this percentage of 42% of patients with amenorrhea which was obtained here from 3 months, whilst the populations are comparable in terms of age, weight and length of time since the menopause. In addition, there exists in the previous study, an estrogen effect which is not found in this other study. On the other hand, this study reveals a dosage effect of progestative during the last 9 months of treatment (the lower the dose of progestative the better the cycle is controlled).

Finally, it is interesting to note that no correlation exists between the existence of an amenorrhea at 6 months and the endometrial thickness measured by endovaginal echography; this thickness varying by +1.6 mm on average over 6 months in the 2 treatment groups.

TABLE VI

Characteristics of the patients

| | TOTAL | | GROUP A | | GROUP C | | |
|---|---|---|---|---|---|---|---|
| | N | avg ± week (min:max) | N | avg ± week (min:max) | N | avg ± week (min:max) | P |
| Age | 54 | 54.9 ± 0.6 45:64 | 19 | 53.9 ± 0.8 48:60 | 17 | 54.9 ± 1.1 45:63 | 0.321 |
| Age of amenorrhia (months) | 54 | 56.1 ± 5.0 7:134 | 19 | 48.5 ± 7.7 12:108 | 17 | 50.7 ± 7.7 11:121 | 0.309 |
| Weight (kg) | 54 | 60 ± 1.1 42:85 | 19 | 61.6 ± 1.2 51:70 | 17 | 60.8 ± 2.2 12:76 | 0.149 |
| Height | 54 | 1.61 ± 0.01 1.47:1.75 | 19 | 1.62 ± 0.01 1.57:1.75 | 17 | 1.61 ± 0.02 1.47:1.75 | 0.449 |
| Quetelet's index (kg/m$^2$) | 54 | 23.1 ± 0.4 17.1:31.2 | 19 | 23.3 ± 0.4 19.7:25.6 | 17 | 23.5 ± 0.7 17.5:28.7 | 0.3182 |
| SBP (mmHg) | 54 | 123.9 ± 1.5 100:140 | 19 | 127.9 ± 2.5 110:140 | 17 | 121.2 ± 0.5 110:140 | 0.136 |
| DBP (mmHg) | 54 | 74.6 ± 1.2 60:90 | 19 | 76.8 ± 2 60:90 | 17 | 73.5 ± 2.3 60:90 | 0.386 |

| | TOTAL | | GROUP A | | GROUP C | | |
|---|---|---|---|---|---|---|---|
| H.R.T. | N | % | N | % | N | % | P |
| Previous HRTs | | | | | | | |
| yes | 17 | 31.5% | 9 | 47.4% | 14 | 82.3% | |
| no | 37 | 68.5% | 10 | 52.6% | 8 | 17.7% | 0.046 |

HRT = Hormone Replacement Therapy
SBP = Systolic Blood Pressure
DBP = Diasystolic Blood Pressure

What is claimed is:

1. A method of treating estrogenic deficiencies in post menopausal women while further avoiding the appearance of osteoporosis and withdrawal bleeding, comprising continuously without interruption administering to said women a composition containing from 0.5 to 3 mg of an estrogen selected from the group consisting of free and esterified estradiol and 1.5 to 3.75 mg of nomegestrol acetate by daily dose.

2. The method of claim 1 wherein the estrogen is an ester of estradiol.

3. The method of claim 1 wherein the composition contains 1.5 mg of free estradiol by daily dose.

4. The method of claim 1 wherein the composition contains 2 mg of ester of estradiol by daily dose.

5. The method of claim 1 wherein the composition contains 2.5 mg of nomegestrol acetate by daily dose.

6. The method of claim 1 wherein the composition is administered orally.

* * * * *